United States Patent [19]

Skuballa et al.

[11] 4,364,950
[45] Dec. 21, 1982

[54] 5-CYANO-PROSTACYCLIN DERIVATIVES AND USE AS MEDICINES

[75] Inventors: Werner Skuballa; Helmut Vorbrüggen; Bernd Radüchel; Jorge Casals-Stenzel; Ekkehard Schillinger; Michael H. Town, all of Berlin, Fed. Rep. of Germany

[73] Assignee: Schering Aktiengesellschaft, Berlin, Fed. Rep. of Germany

[21] Appl. No.: 317,621

[22] Filed: Nov. 2, 1981

[30] Foreign Application Priority Data

Oct. 31, 1980 [DE] Fed. Rep. of Germany ....... 3041602

[51] Int. Cl.³ .............. A61K 31/557; C07D 307/935
[52] U.S. Cl. ................................. 424/263; 424/275; 424/285; 542/426; 546/269; 549/60; 549/414; 549/465
[58] Field of Search .............. 260/346.22, 346.73, 260/345.9; 542/426; 549/60; 546/269; 424/285, 263, 275

[56] References Cited

U.S. PATENT DOCUMENTS 4,219,479 8/1980 Vorbrüggen et al. ......... 260/346.22
4,235,930 11/1980 Skuballa et al. ............... 260/346.22

Primary Examiner—Henry R. Jiles
Assistant Examiner—Bernard Dentz
Attorney, Agent, or Firm—Millen & White

[57] ABSTRACT 5-cyano-prostacyclins of the formula

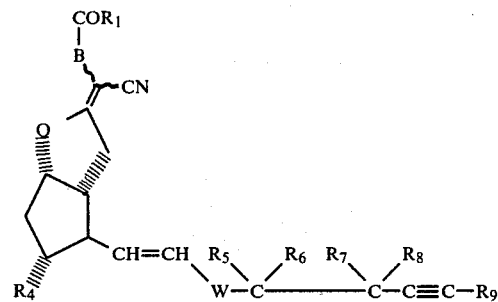

wherein
$R_1$ is $OR_2$ or $NHR_3$; $R_2$ and $R_3$ each independently is (a) H, (b) $C_{1-10}$-alkyl, (c) $C_{1-10}$-alkyl substituted by halo, $C_{1-4}$-alkoxy or phenyl, 1-naphthyl or 2-naphthyl, each optionally substituted as defined below, (d) $C_{4-10}$-cycloalkyl, (e) $C_{4-10}$-cycloalkyl substituted by $C_{1-4}$-alkyl, (f) phenyl, 1-naphthyl or 2-naphthyl, (g) phenyl, 1-naphthyl or 2-naphthyl substituted by 1-3 halogen atoms, phenyl, 1-3 alkyl groups of 1-4 C atoms each, or a chloromethyl-, fluoromethyl-, trifluoromethyl-, carboxyl-, hydroxy- or alkoxy-group of 1-4 C atoms, or (h) an aromatic, 5- or 6-membered heterocyclic ring containing one hetero atom which is O, N or S, the remaining atoms being carbon; $R_3$ also possibly being an acyl group of a $C_{1-15}$-hydrocarbon carboxylic or sulfonic acid;
B is straight chain or branched alkylene of 2-10 C atoms;
W is hydroxymethylene or

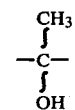

wherein the OH group may be in the alpha or beta position, and is optionally modified by replacement of the H atom of the OH with an ether or acyl group which is conventional for such replacements in prostaglandins and which is readily cleavable at physiological pH's;
$R_4$ is hydroxy, optionally modified as described for W above;
$R_5$, $R_6$, $R_7$ and $R_8$ each independently is hydrogen, alkyl of 1-5 C atoms or methoxy; and
$R_9$ is alkyl of 1-5 C atoms or for compounds wherein $R_2$ is H, the salts thereof with physiologically compatible bases have valuable pharmacological properties, e.g., hypertonic and bronchodilatory activities.

23 Claims, No Drawings

5-CYANO-PROSTACYCLIN DERIVATIVES AND USE AS MEDICINES

BACKGROUND OF THE INVENTION

The present invention concerns new prostacyclin derivatives, processes for their preparation and their use as medicines.

Prostacyclin (PGI$_2$) is one of the main factors in blood platelet aggregation. It acts in a dilating manner on various blood vessels (Science 196, 1072) and therefore can be considered as a means for lowering blood pressure. PGI$_2$, however, lacks the stability required for a medicine. Thus its half-life value at physiological pH values and at room temperature is only a few minutes. Prostacyclin derivatives are known from the German Offenlegungsschrift No. 27 53 244 and its U.S. equivalent U.S. Pat. No. 4,219,479 which have stability substantially increased by a cyano residue at the enolether double bond. However, even these compounds are in need of enhanced properties.

SUMMARY OF THE INVENTION

Accordingly, it is an object of this invention to produce prostacyclin derivatives with enhanced properties.

Upon further study of the specification and appended claims, further objects and advantages of this invention will become apparent to those skilled in the art.

These objects have been attained by providing 5-cyanoprostacyclins of formula I

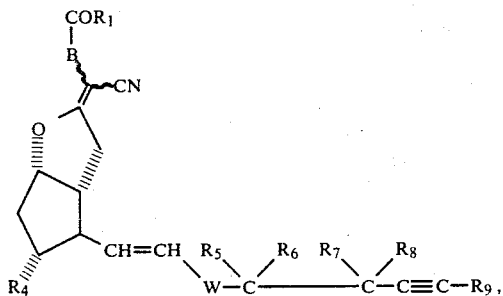

wherein
R$_1$ is OR$_2$, wherein R$_2$ is hydrogen, alkyl, cycloalkyl, aryl or a heterocyclic residue; or R$_1$ is NHR$_3$ wherein R$_3$ is an acid residue or hydrogen, alkyl, cycloalkyl or a heterocyclic residue all as defined for R$_2$,
B is a straight chain or branched alkylene group of 2-10 carbon atoms;
W is a free or functionally modified hydroxymethylene group or a free or functionally modified

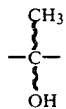

group, where the OH group may be in the alpha or beta position,
R$_4$ is a free or functionally modified hydroxy group,
R$_5$, R$_6$, R$_7$ and R$_8$ each independently is hydrogen, alkyl of 1-5 C atoms or methoxy,
R$_9$ is alkyl of 1-5 C atoms, and
when R$_2$ is hydrogen, physiologically compatible salts of such compounds with bases.

DETAILED DISCUSSION

It has been found that the selectivity, the duration of effectiveness and the activity of 5-cyanoprostacyclins can be still further improved by introducing a triple bond in the 18-position, optionally with additional alkyl or methoxy groups in the lower chain of the 5-cyano-prostacyclin.

Suitable alkyl groups R$_2$, among others, include straight chain or branched alkyl groups of 1-10 C atoms, for instance, methyl, ethyl, propyl, butyl, isobutyl, tertbutyl, pentyl, neopentyl, heptyl, hexyl, decyl and the like. The alkyl groups R$_2$ also may be monosubstituted or polysubstituted by halogen atoms, e.g., Br, Cl, F, alkoxy groups of 1-4 C atoms, optionally substituted aryl groups, or dialkylamino or trialkylammonium each of 1-4 C atoms in each alkyl. Preferred are monosubstituted alkyl groups. Illustrative substituents, for instance, include fluorine, chlorine, bromine, phenyl, dimethylamino, diethylamino, methoxy and ethoxy. Preferred R$_2$ alkyl groups are those of 1-4 C atoms such as methyl, ethyl, propyl, dimethylaminopropyl, isobutyl, butyl and the like.

Suitable R$_2$ aryl groups include substituted and unsubstituted aryl groups, for instance phenyl, 1-naphthyl and 2-naphthyl which each can be substituted by 1-3 halogen atoms, phenyl, 1-3 alkyl groups of 1-4 C atoms each, or a chloromethyl-, fluoromethyl-, trifluoromethyl-, carboxyl-, hydroxy- or alkoxy-group of 1-4 C atoms. Preferred is substitution in the 3- and 4-position of the phenyl ring, for instance by fluorine, chlorine, alkoxy or trifluoromethyl or in the 4-position by hydroxy.

Suitable R$_2$ cycloalkyl groups may contain 4-10, preferably 5 or 6 C atoms in the ring. The rings can optionally be substituted by alkyl groups of 1-4 C atoms. Suitable groups for instance include cyclopentyl-hexyl, cyclohexyl, methylcyclohexyl and adamantyl.

Suitable R$_2$ heterocyclic groups include heterocycles of 5 and 6 ring members, among which those which are aromatic and have one ring heteroatom such as nitrogen, oxygen or sulfur are especially preferred. Suitable groups include 2-furyl, 2-thienyl, 2-pyridyl, 3-pyridyl, 4-pyridyl, among others.

Suitable acid residues R$_3$ are acyl groups which are physiologically compatible. Preferred acids are organic carboxylic acids and sulfonic acids of 1-15 C atoms belonging to the aliphatic, cycloaliphatic, aromatic, aromatic-aliphatic and heterocyclic series. These are hydrocarbons or, equivalently contain other atoms. These acids may be saturated, unsaturated and/or polybasic and/or substituted in conventional manner. All are equivalent for the purpose of this invention. Illustrative substituents include C$_1$–C$_4$ alkyl, hydroxy, C$_1$–C$_4$ alkoxy, oxo, amino or halogen.

Illustratively, suitable carboxylic acids include: formic acid, acetic acid, propionic acid, butyric acid, isobutyric acid, valeric acid, isovaleric acid, capronic acid, enanthic acid, caprylic acid, pelargonic acid, capric acid, undecylic acid, lauric acid, tridecylic acid, myristic acid, pentadecylic acid, trimethyl acetic acid, diethyl acetic acid, tert-butyl acetic acid, cyclopropyl acetic acid, cyclopentyl acetic acid, cyclohexyl acetic acid, cyclopropane carboxylic acid, cyclohexanoic carboxylic acid, phenyl acetic acid, phenoxy acetic acid, methoxy acetic acid, ethoxy acetic acid, mono-, di- and trichloroacetic acid, amino acetic acid, diethylamino acetic acid, piperidino acetic acid, morpholino acetic acid, lactic acid, succinic acid, adipic acid, benzoic acid, benzoic acids substituted by halogen, trifluoromethyl, hydroxy, alkoxy or carboxy, nicotinic acid, isonicotinic acid, furane-2-carboxylic acid, cyclopentyl propionic acid, etc. Especially preferred acyl residues are those with up to 10 C atoms. Suitable sulfonic acids for instance include methane sulfonic acid, ethane sulfonic acid, isopropane sulfonic acid, beta-chloroethane sulfonic acid, butane sulfonic acid, cyclopentyl sulfonic acid, cyclohexane sulfonic acid, benzene sulfonic acid, p-toluene sulfonic acid, p-chlorobenzene sulfonic acid, N,N-dimethylamino sulfonic acid, N,N-diethylamino sulfonic acid, N,N-bis-(beta-chloroethyl)-amino sulfonic acid, N,N-diisobutylamino sulfonic acid, N,N-dibutylamino sulfonic acid, pyrrolidone-, piperidino-, piperazino-, N-methylpiperazino- and moropholino-sulfonic acid.

For the other $R_3$ possibilities, the foregoing discussion of $R_2$ groups applies. The hydroxy groups in $R_4$ and in W can be functionally modified, for instance by etherification or esterification. The free or modified hydroxy groups in W can be in the alpha or beta positions, free hydroxy groups being preferred. Suitable ether and acyl residues are known to those skilled in the art and produce overall compounds which are physiologically active and readily cleavable in vivo, e.g., of physiological pH's. Preferred ether residues include tetrahydropyranyl, tetrahydrofuranyl, alpha-ethoxyethyl, trimethyl silyl, dimethyltert-butylsilyl or tribenzyl-silyl. Suitable acyl residues include $C_1-C_4$ alkanoyl residues such as acetyl, propionyl, butyryl or benzoyl. Suitable alkylene groups B include straight chain alkylene groups of 1–10 and especially 1–5 C atoms such as methylene, ethylene, trimethylene, tetramethylene, pentamethylene etc.

$R_5$, $R_6$, $R_7R_8$ and $R_9$ alkyl groups include straight chain or branched alkyl of 1–5 C atoms such as methyl, ethyl, propyl, isopropyl, butyl, isobutyl, tert-butyl, pentyl and neopentyl. Preferred residues are methyl and ethyl.

Suitable inorganic and organic bases are known to those skilled in the art for forming physiologically compatible salts. Illustratively the following can be cited, alkli metal hydroxides such as sodium and potassium hydroxide, alkaline earth hydroxides such as calcium hydroxide, ammonia, amines such as ethanolamine, diethanolamine, triethanolamine, N-methylglucamine, morpholine, tris-(hydroxymethyl)-methylamine etc.

The present invention moreover concerns a process for producing the prostacyclin derivatives of this invention comprising
oxidizing a compound of formula II,

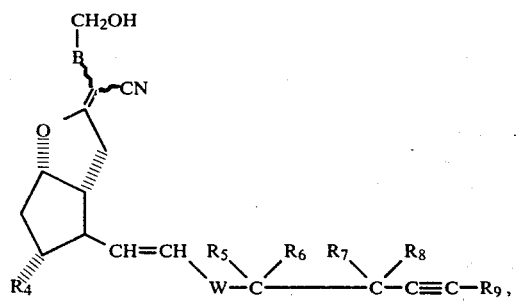

wherein,
B, $R_4$, $R_5$, $R_6$, $R_7$, $R_8$, W and $R_9$ are as defined above and the free hydroxy groups in $R_4$ and W are protected, and, optionally, in arbitrary sequence, separating isomers, releasing protected hydroxy groups and/or esterifying or etherifying free hydroxy groups, and/or esterifying a 1-free carboxyl group and/or saponifying an esterified carboxyl group, and/or reacting a carboxyl group in the 1-position of a resultant compound with a compound of formula III $$O=C=N-R_3 \qquad \text{III,}$$

wherein $R_3$ is defined as above and/or converting such a carboxyl group into a physiologically compatible salt using a corresponding base.

The oxidation of the 1-hydroxy group can be carried out by methods known in the art. The following, for instance, may be used as oxidizers: pyridinium chromate (Tetrahedron Letters, 1979, 399), Jones reagent (J. Chem. Soc. 1953, 2555) or platinum/oxygen (Adv. in Carbohydrate Chem. 17, 169, [1962]). All of these disclosures are incorporated by reference herein.

The oxidation with pyridinium dichromate is carried out at temperatures of 0° to 100° C., preferably of 20° to 40° C. in a solvent inert with respect to the oxidizer, for instance dimethyl formamide.

The oxidation with the Jones reagent is carried out at temperatures of −40° C. to +40° C., preferably of 0° to 30° C. in e.g., acetone as the solvent.

The oxidation with platinum/oxygen is carried out at temperatures of 0° to 60° C., preferably 20° to 40° C., in a solvent inert with respect to the oxidizer, for instance acetic acid.

The saponification of the prostacyclin esters is carried out by methods known to the expert, for instance using basic catalysts.

Introducing the ester group $-OR_2$ as $R_1$, where $R_2$ is alkyl of 1–10 C atoms, can be carried out by methods known in the art. For instance, the carboxy compounds can be reacted in a manner known per se with diazo hydrocarbons. The esterification with diazo hydrocarbons for instance is carried out by mixing a solution of the diazo hydrocarbon in an inert solvent, preferably in diethylether, with the carboxy compound in the same or in another inert solvent, for instance, methylene chloride. When the reaction is completed after 1 to 30 minutes, the solvent is removed and the ester is purified in conventional manner. The diazo alkanes required for the reactions either are known or can be prepared by known methods (See, e.g., Org. Reactions vol. 8, pp 389–394, 1954 whose disclosure is incorporated by reference herein.)

The introduction of the ester group $-OR_2$ for $R_1$ wherein $R_2$ is a substituted or an unsubstituted aryl group can also be conducted by methods known in the art. For instance, the carboxy compounds can be reacted with the corresponding aryl-hydroxy compounds using dicyclohexylcarbodiimide in the presence of a suitable base, for instance pyridine or triethylamine, in an inert solvent. Appropriate solvents are methylene chloride, ethylene chloride, chloroform, ethyl acetate, tetrahydrofuran, preferably chloroform. The reaction is carried out at temperatures of −30° C. to +50° C., preferably at about +10° C.

The prostacyclin derivatives of formula I wherein $R_1$ is hydroxy can be converted into salts by means of neutralization using suitable amounts of corresponding inorganic bases. For instance, when the corresponding prostacyclin acid is dissolved in water containing a stoichiometric quantity of base, and after the water is evaporated or after a water miscible solvent is added, for instance alcohol or acetone, the solid inorganic salt is obtained.

Likewise, an amine salt can be prepared in conventional manner. For example, the prostacyclin acid can be dissolved for instance in a suitable solvent such as ethanol, acetone, diethylether or benzene and at least a stoichiometric quantity of the amine added to this solution. Ordinarily, the salt is obtained in solid form or is conventionally isolated after evaporating the solvent.

Functional modification of the free OH groups in $R_4$ or W can also be conducted by methods known in the art. The introduction of the ether protective groups can be implemented, for instance, by reaction with dihydropyran in methylene chloride or chloroform while using an acidic condensing agent such as p-toluol sulfonic acid. The dihydropyran is used in excess, preferably from four-fold to ten-fold of the theoretically required amount. The reaction ordinarily is terminated after 15–30 minutes at 0° C.–30° C.

Acyl protective groups can be introduced by reacting a compound of formula I in a manner known per se with a carboxylic acid derivative such as an acid chloride, acid anhydride, among others.

The freeing of a functionally modified OH group to produce compounds of formula I can also be accomplished by known methods. For instance, splitting off ether protective groups can be performed in an aqueous solution of an organic acid, for instance acetic acid, propionic acid, among others, or in an aqueous solution of an inorganic acid such as hydrochloric acid. To improve solubility, an inert, water-miscible solvent can be added where appropriate. Suitable organic solvents, for instance, include alcohols such as methanol and ethanol, and ethers such as dimethoxyethane, dioxane and tetrahydrofuran. Tetrahydrofuran is preferred. The splitting is preferably carried out at temperatures of 20° to 80° C.

The splitting off of the silylether protective groups, for instance, can be carried out with tetrabutylammonium or with KF in the presence of a crown ether. Suitable solvents, for instance, include tetrahydrofuran, diethylether, dioxane, methylene chloride etc. The splitting is preferably carried out at temperatures of 0° to 80° C.

Saponification of acyl groups can be carried out for instance with alkali or alkaline earth metal carbonates or hydroxides is an alcohol or in the aqueous solution of an alcohol. Suitable alcohols include aliphatic alcohols, for instance methanol, ethanol, butanol etc., preferably methanol. Potassium and sodium salts, preferably potassium salts, are examples of such alkali metal carbonates and hydroxides. Suitable alkaline earth carbonates and hydroxides for instance include calcium carbonate, calcium hydroxide and barium carbonate. The reaction usually occurs at −10° C. to 70° C., preferably at 25° C.

The reaction of a compound of formula I wherein $R_2$ is hydrogen with an isocyanate of formula III may be performed with the addition of a tertiary amine such as triethylamine or pyridine. The reaction can be carried out without a solvent or in an inert solvent, preferably acetonitrile, tetrahydrofuran, acetone, dimethylacetoamide, methylene chloride, diethylether, benzene, toluene, dimethylsulfoxide, at temperatures above or below room temperature, for instance from −80° C. to 100° C., preferably at 0° to 30° C.

If the initial product contains OH groups in the prostane residue, these OH groups are also reacted. If, end products are desired which contain free hydroxyl groups in the prostane residue, then corresponding starting materials having these OH groups temporarily protected by preferably easily splitting ether or acyl residues, are used.

The compounds of formula II serving as starting materials can be prepared, for instance, by reaction, in a manner known per se, of an aldehyde of formula IV (E. J. Corey et al., JACS 91, 5675 [1969]; E. W. Yankee et al., JACS 96, 5865 [1974], which are incorporated by reference herein),

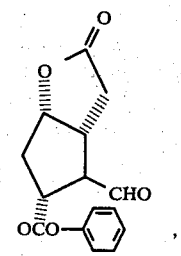

IV with a phosphonate of formula V

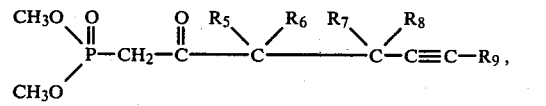

V wherein $R_5$, $R_6$, $R_7$, $R_8$ and $R_9$ are defined as above, in an olefin forming reaction to form a ketone of formula VI

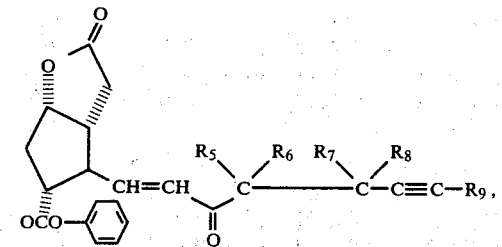

VI

After reducing the 15-keto group with zinc borohydride or reaction with alkylmagnesium bromide or alkyllithium, the epimeric 15-alpha- and 15-beta-alcohols (PG numbering) are obtained. If desired, these may be separated and, where appropriate, can be converted by esterification or etherification into the compounds of formula VII:

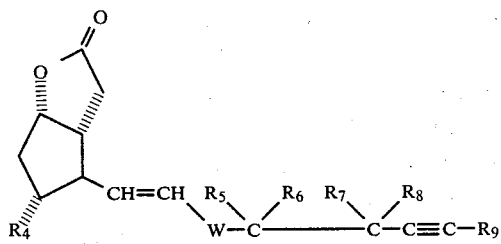

By reacting the lactone of formula VII with a carbanion prepared from a nitrile of formula VIII and lithium diisopropylamide

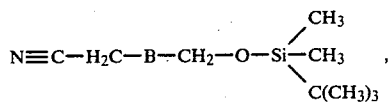

and then treating the crude product with a catalytic quantity of an acid, for instance boron trifluoride or p-toluene sulfonic acid and thereafter protecting free hydroxy groups by esterification, the enolether of formula IX can be produced. See, e.g., German patent application No. 30 41 601.4 of Oct. 31, 1980, and corresponding U.S. application Ser. No. 317,690, filed on Nov. 2, 1981, the disclosures of which are incorporated by reference herein.

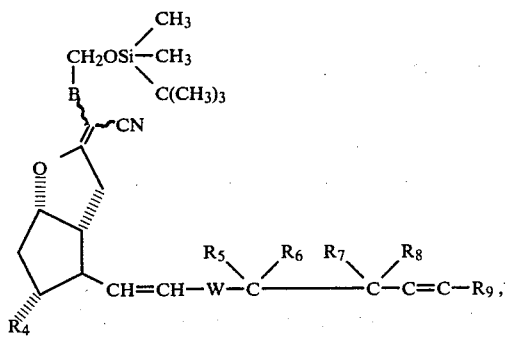

After conventionally splitting off the silylether protective group, compounds of formula II are obtained. Depending on the nature of the functionally modified hydroxy groups in W and $R_4$, the silylether splitting step is carried out with tetrabutylammonium fluoride or with an aqueous solution of an organic acid, for instance acetic acid.

The cyanoprostacyclins, isomeric at the cyano double bonds, that are prepared by the above reactions can be separated by conventional separation methods such as column chromatography or thin-film chromatography.

The phosphonates of formula V can be prepared in a manner known per se by reacting an alkyl halide of formula X

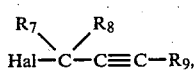

with the dianion of a phosphonate of formula XI

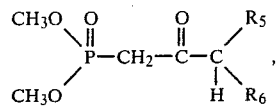

The phosphonates of formula V can also be prepared by reacting the anion of methyl phosphoric acid dimethylester with an ester of formula XII

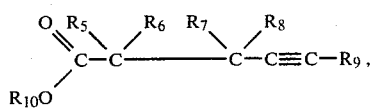

wherein $R_5$, $R_6$, $R_7$, $R_8$ and $R_9$ are defined as above and $R_{10}$ is alkyl of 1–5 C atoms. It can be obtained for instance from the corresponding malonic acid by alkylating with a halide of formula X and ensuing decarboalkoxylation.

The nitrile of formula VIII can be prepared, for instance, from 1,5-pentanediol by selective silylation, tosylation and ensuing reaction with potassium cyanide.

The compounds of this invention are effective to lower blood pressure and also are bronchodilatory. They are furthermore active in inhibiting thrombocyte aggregation.

Accordingly the new prostacyclin derivatives of formula I represent valuable pharmaceutical substances. Compared to the corresponding prostaglandins and conventional prostacyclins and for a similar effective spectrum, they evince higher specificity and, most importantly, a substantially longer-term effectiveness. Compared with $PGI_2$ they are characterized by higher stability. The high tissue specificity of the new prostaglandins can be shown by investigating smooth-muscle organs such as the guinea-pig ileum or the isolated rabbit trachea, where a substantially lesser stimulation is evinced than when natural prostaglandins of the E, A or F type are used.

The new prostaglandin analogs of this invention have properties typical of prostaglandins, e.g., they are useful in mammals, including humans, for instance, for lowering peripheral arterial and coronary vascular resistance, for inhibition of thrombocyte aggregation and dissolution of platelet thrombi, for myocardial cyto protection and hence lowering of systemic blood pressure without simultaneously lowering the systolic volume and coronary blood supply; for treatment of strokes, prophylaxis and therapy of coronary heart ailments, coronary thrombosis, heart infarct, peripheral arterial ailments, arteriosclerosis and thrombosis, shock therapy, inhibition of broncho-constriction, inhibition of stomach acid secretion and cyto production of the stomach lining and intestinal mucous membrane; for lowering of the pulmonary vascular resistance and pulmonary blood pressure and enhancement of renal blood supply; they also have antiallergenic properties; they can also be used as substitutes for heparin or used as adjuvants in the dialysis of hemofiltration; they are useful for conservation of blood plasma preserves, in particular, blood platelet preserves, inhibition of labor pains, treatment of pregnancy toxicosis, increase in cerebral blood supply etc. Moreover the new prostaglandin analogs evince antiproliferative properties.

The conventional prostacyclin compounds described above, are all potent in causing multiple biological responses even at low doses. Moreover, for many applications, these prostacyclins have an inconveniently short duration of biological activity. In striking contrast, the novel prostacyclin analogs of this invention are substantially more selective with regard to potency in causing prostacyclin-like biological responses, and have a substantially longer duration of biological activity. Accordingly, each of these novel prostacyclin analogs is surprisingly and unexpectedly more useful than one of the corresponding prostacyclins of the prior art for at least one of the pharmacological purposes indicated above, because it has a different and narrower spectrum of biological potency than the known compounds, and therefore is more specific in its activity and causes smaller and fewer undesired side effects than when the known compound is used for the same purpose. Moreover, because of its prolonged activity, fewer and smaller doses of the novel prostacyclin analog are frequently effective in attaining the desired result.

The dosage of the compounds of this invention generally is 1 to 1500 micrograms/kg/day for human patients. The unit dose for the pharmaceutically acceptable vehicle generally is 0.01 to 100 mg.

When intraveneously injected into awake, hypertonic rats, in doses of 5,20 and 100 micrograms/kg of body weight, the compounds of this invention evince a more pronounced blood-pressure lowering and longer-lasting effect than $PGE_2$ and $PGA_2$, without triggering diarrhea as in the case of $PGE_2$ or cardial arrythmia as in the case of $PGA_2$.

When intravenously injected into anesthesized rabbits, the compounds of the invention, compared with $PGE_2$ and $PGA_2$, evince a more pronounced and substantially longer-lasting drop in blood pressure, without affecting other smooth-muscular organs or organ functions.

Sterile, injectable, aqueous or oily solutions are used for parenteral administration. Tablets, dragees or capsules are suited among others for oral application.

The invention also applies to medicines based on the compounds of formula I and conventional excipients and accessory substances.

The substances of the invention, for example, can be used in conjunction with the known and conventional auxiliary pharmaceutical substances, for instance, to prepare blood-pressure lowering medicaments.

The pharmacologically active compounds of formula I can be processed in accordance with conventional methods of galenic pharmacy to product medicinal agents, especially for oral administration. Conventional excipients are pharmaceutically acceptable organic or inorganic carrier sustances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, which are sterile and injectable, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The administration of the compounds of this invention can be conducted in accordance with that for known prostacyclins such as Prostacyclin (PG $I_2$) except that advantage can be taken of their advantageous properties.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-cyano-18,19-tetradehydro-prostacyclin

A solution of 325 mg of 5-cyano-2-descarboxy-2-hydroxymethyl-18,19-tetrahydroprostacyclin-11,15-diacetate in 5 ml of dimethylformamide is reacted with 880 mg pyridinium dichromate and the mixture is stirred for 29 h at room temperature. It is thereupon diluted with 60 ml of water and these extractions follow, in each case with 50 ml of a mixture of ether/pentane (2/1); the organic extract is shaken three times with 20 ml of water in each case; drying is carried out over magnesium sulfate; and concentration is carried out by vacuum evaporation. After the residue is filtered through silica gel, ether/acetic-acid (1/1) is used to obtain 240 mg of 5-cyano-18,19-tetradehydro-prostacyclin-11,15-diacetate.

The acetate is dissolved in 12 ml of methanol and reacted with 280 mg of water free potassium carbonate which is followed by stirring for 16 h at room temperature. Thereupon, 10% citric acid solution is used to acidify to a pH of 5, methylene chloride is used to extract, the organic extract is agitated three times with brine and dried over magnesium sulfate. The evaporation residue is chromatographed with methylene-chloride/isopropanol (85/15) on silica gel. 170 mg of the title compound is obtained in the form of a colorless oil.

IR: 3600, 3420 (wide), 2920, 2200, 1713, 1650, 970/cm.

The initial material for the title compound is prepared as follows:

(1a)
(1S,5R,6R,7R)-6-[(E)-(3S)-3-benzoyloxy-1-octene-6-ynyl]-7-benzoyloxy-2-oxabicyclo[3.3.0]-octane-3-one 2.3 ml of benzoyl chloride is added to a solution of 3.8 g of (1S,5R,6R,7R)-6-[(E)-(3S)-3-hydroxy-1-octene-6-ynyl]-7-benzoyloxy-2-oxabicyclo[3.3.0]-octane-3-one (described in the German Offenlegungsschrift No. 27 29 960) at ice bath temperature, the mixture being stirred for 18 h at room temperature. Thereupon the mixture is reacted with 1 ml of water, stirred for 2 h, and diluted with 250 ml of ether, agitated once with water, twice with 10% sulfuric acid, once with 5% sodium bicarbonate solution and three times with water. Drying takes place over magnesium sulfate, concentration is carried out by vacuum evaporation, and the residue is filtered on silica gel. Using ether/hexane (8/2), 4.6 g of the dibenzoate is obtained as a colorless oil.

IR: 2970, 2923, 1770, 1715, 1602, 1585, 1270, 968/cm.

(1b)
5-cyano-2-descarboxy-2-(dimethyl-tert-butylsiloxymethyl)-18,19-tetrahydro-prostacyclin-11,15-diacetate 2.55 ml of diisopropylamine is reacted at −25° C. within 15 minutes with 11.8 ml of 1.53 molar solution of butyl-lithium in hexane; stirring proceeds for 1 h at −25° C. The material then is reacted with 3.2 ml of hexamethyl phosphoric acid triamide, and into this mixture is dripped—within 30 minutes and at a temperature of −70° C.—a solution of 4.1 g of 6-(dimethyl-tert-butylsilyloxy)-hexane-nitrile in 4 ml of tetrahydrofuran. This substance is stirred for 20 minutes at −70° C., whereupon a solution of 2.4 g of the dibenzoate made per example (1a) in 15 ml of ether and 15 ml of tetrahydrofuran is added; stirring proceeds for 20 minutes, whereupon the reaction mixture is acidified to a pH of 5 by pouring in a 10% citric acid solution. Extraction is carried out using ether, the organic phase is washed with water until it is neutral, drying takes place over magnesium sulfate, and the evaporation residue is filtered with acetic acid using silica gel. In this manner, 1.7 g of the reaction product of the organo-metallic conversion is obtained as a 11,15-dihydroxy compound.

In order to split off water, the reaction product of the above-described conversion is dissolved in 80 ml of absolute ether, 50 ml of a diluted etheric borotrifluoride solution (prepared by diluting 0.5 ml of 45% borotrifluoride etherate solution in 45 ml of absolute ether) is added and the mixture is stirred for 1 h at room temperature. Thereupon, 5% sodium bicarbonate solution is poured in, the material is washed with water until neutral and dried over magnesium sulfate and concentrated by evaporation in vacuum.

The residue is dissolved in 6 ml of pyridine, 2 ml of acetic acid anhydride is added, and the mixture is stirred at room temperature for 16 h. Thereupon, it is concentrated by evaporation in vacuum and the residue is chromatographed on silica gel. Using hexane/ether (3/2) first 720 mg of the title compound are obtained (5E configuration), and as a more polar component 610 mg of the isomeric (5Z)-5-cyano-2-descarboxy-2-(dimethyl-tert-butylsiloxymethyl)-18,19-tetrahydro-prostacyclin-11,15-diacetate.

IR: 2953, 2930, 2860, 2200, 1732, 1651, 1240, 970, 970, 835/cm.

(1c)
5-cyano-2-decarboxy-2-hydroxymethyl-18,19-tetradehydroprostacyclin-11,15-diacetate 0.7 g of the diacetate prepared per example (1b) is stirred together with a mixture of acetic-acid/water/tetrahydrofuran (65/35/10) for 16 h at room temperature and thereupon is vacuum-evaporated. Following chromatography of the residue on silica gel, 530 mg of the compound of the title is obtained in the form of colorless oil using ether/acetic-acid (1/1).

IR: 3610, 2960, 2200, 1732, 1650, 1240, 970/cm.

(1d) 6-(dimethyl-tert-butylsilyloxy)-hexane nitrile

Working at an ice bath temperature, 90.5 g of dimethyl-tert-butylsilyl chloride is added to a solution of 62.5 g of 1.5 pentanediol and 102 g of imidazole in 100 ml of dimethylformamide and the mixture is stirred at 0° C. for 16 h. Then 900 ml of water is poured on the substance, which is extracted three times, each time with 500 ml of a mixture of hexane/ether (1/1) and the organic extract is washed until neutral with water and dried over magnesium sulfate. This is followed by vacuum evaporation and the residue is distilled in 0.6 torr vacuum. 55 g of the monosilylether is obtained at 76°–80° C. as a colorless liquid.

To tosylate, the substrate is dissolved in 185 ml of pyridine, 74 g of p-toluene sulfonic acid chloride is added and stirring proceeds for 16 h at room temperature. Thereupon, the substance is reacted with 10 ml of water, stirred for 3 hours, diluted with 1.3 liters of ether, sequentially shaken with 10% sulfuric acid with water, with 5% sodium bicarbonate solution and with water. The substance then is dried over magnesium sulfate and vacuum evaporated.

The residue is dissolved in 185 ml of dimethyl sulfoxide, 22 g of sodium cyanide is added and the mixtrue is stirred for 18 h at 80° C. under argon. Thereupon, it is reacted with 700 ml of water, extracted three times each time with 400 ml of a mixture of ether/hexane (1/1), the organic extract is then washed until neutral with water and dried over magnesium sulfate. This is followed by vacuum evaporation and vacuum distillation of the residue in a 0.1 torr vacuum. 43 g of the title compound is obtained at 75°–77° C. as a colorless liquid.

IR: 2930, 2855, 2242, 1250, 1095, 830/cm.

EXAMPLE 2

5-cyano-(16RS)-16-methyl-18,19-tetrahydroprostacyclin

A mixture of 670 mg of 5-cyano-2-descarboxy-2-hydroxymethyl-(16RS)-16-methyl-18,19-tetrahydro-prostacyclin-11,15-diacetate, 1.8 g of pyridinium dichromate and 10 ml of dimethylformamide is stirred for 30 h at room temperature. Then it is diluted with water, extracted with a mixture of ether/pentane (2/1), the organic extract is washed with water, dried over magnesium sulfate and vacuum-evaporated. After filtering the residue with silica gel, the use of ether/acetic acid (1/1) yields 460 mg of 5-cyano-(16RS)-16-methyl-18,19-tetradehydro-prostacyclin-11,15-diacetate.

The diacetate is stirred for 16 h at room temperature in 22 ml of methanol with 550 mg of potassium carbonate (water-free). Then it is acidified with 10% citric acid solution to a pH of 5, extracted with methylene chloride, the organic extract is agitated with brine 3 times and the mixture is dried over magnesium sulfate. The evaporation residue is chromatographed with methylene-chloride/isopropanol (85/15) on silica gel. 220 mg of the title compound is obtained as oil.

IR: 3610, 3400 (wide), 2925, 2200, 1712, 1650, 972/cm.

The initial material for the above title compound is prepared as follows:

(2a)
(1S,5R,6R,7R)-6-[(E)-(3S,4RS)-3-benzoyloxy-4-methyl-1-octene-6-ynyl]-7-benzoyloxy-2-oxabicyclo[3.3.0]-octane-3-one Similarly to example (1a), 4.9 g of the title compound is obtained as a colorless oil form 4.1 g of (1S,5R,6R,7R)-6-[(E)-(3S,4RS)-3-hydroxy-4-methyl-1-octene-6-ynyl]-7-benzoyloxy-2-oxabicyclo[3.3.0]-octane-3-one.

IR: 2965, 2920, 1770, 1715, 1602, 1585, 1450, 1315, 2170, 1110, 969/cm.

(2b)
5-cyano-2-descarboxy-2-(dimethyl-tert-butylsilyloxymethyl)-(16RS)-16-methyl-18,19-tetradehydroprostacyclin-11,15-diacetate 12 ml of a 1.5 molar solution of butyl lithium in hexane is dripped into 2.6 ml of diisopropylamine at −25° C., the mixture then is stirred for 1 h and next reacted with 3.3 ml of hexamethyl phosphoric acid triamide. A solution of 4.2 g of 6-(dimethyl-tert-butylsiloxy)-hexane nitrile in 5 ml of tetrahydrofuran is dripped at −70° C. into the above mixture, to be followed by stirring for 20 minutes at −70° C., and a solution of 2.5 g of the dibenzoate prepared per example (2a) in 15 ml of ether and 15 ml of tetrahydrofuran is added. After 20 minutes, the reaction mixture is acidified to a pH of 5 by pouring in it a 10% citric acid solution, the substance then being extracted with ether, the organic extract being shaken with water and dried over magnesium sulfate and vacuum-evaporated. The residue is filtered with acetic acid over silica gel. 1.6 g of the reaction product of the organo-metallic conversion is obtained as 11,15-diol which is dissolved in ether and stirred together with 50 ml of a diluted etheric borotrifluoride solution (prepared per example (1b) for 1 h at room temperature. Then 5% sodium bicarbonate solution is poured on, the substance is washed with water until neutral, dried over magnesium sulfate and vacuum evaporated.

The residue is stirred for 16 h at room temperature with 6 ml of pyridine and 2 ml of acetic acid anhydride. Then the substance is vacuum evaporated and the residue is chromatographed on silica gel. Using hexane/ether (3/2), first one obtains 690 mg of the compound of the title (5E configuration), and as the more polar component, 580 mg of the isomeric (5Z)-5-cyano-2-descarboxy-2-(dimethyl-tert-butylsiloxymethyl)-(16RS)-16-methyl-18,19-tetrahydroprostacyclin-11,15-diacetate.

IR: 2955, 2935, 2860, 2200, 1731, 1650, 1240, 970, 835/cm.

(2c)
5-cyano-2-descarboxy-2-hydroxymethyl-(16RS)-16-methyl-18,19-tetradehydroprostacyclin-11,15-diacetate Similarly to example (1c), 480 mg of the title compound is obtained as a colorless oil from 0.6 g of the diacetate prepared per example (2b).

IR: 3600, 3400, 2965, 2860, 2200, 1730, 1651, 1240, 972/cm.

EXAMPLE 3

(5Z)-5-cyano-(16RS)-16-methyl-18,19-tetradehydro-prostacyclin

A mixture of 340 mg of (5Z)-5-cyano-2-descarboxy-2-hydroxymethyl-(16RS)-16-methyl-18,19-tetradehydroprostacyclin-11,15-diacetate, 950 mg of pyridinum dichromate and 5 ml of dimethylformamide is stirred for 28 h at room temperature. This mixture then is diluted with water, extracted with a mixture of the ether/pentane (2/1), the organic extract is shaken with water, dried over magnesium sulfate and vacuum evaporated. After the residue is filtered over silica gel, 220 mg of (5Z)-5-cyano-(16RS)-16-methyl-18,19-tetradehydroprostacyclin-11,15-diacetate is obtained when using ether/acetic-acid (1/1). The diacetate is stirred for 16 h at room temperature in 10 ml of methanol with 280 mg of (water free) potassium carbonate; then it is acidified with 10% citric acid, extracted with methylene chloride; the organic extract next is shaken with water and dried over magnesium sulfate. After the evaporation residue is chromatographed on silica gel, 105 mg of the title compound is obtained using methylene-chloride/isopropanol (85/15), in the form of an oil.

IR: 3600, 3400, 2925, 2200, 1710, 1654, 972/cm.

The initial material for the title compound is prepared as follows:

(3a)
(5Z)-5-cyano-2-descarboxy-2-hydroxymethyl-(16RS)-16-methyl-18,19-tetradehydro-prostacyclin-11,15-diacetate 0.55 g of (5Z)-5-cyano-2-descarboxy-2-(dimethyl-tert-butylsilyloxymethyl)-(16RS)-16-methyl-18,19-tetrahydroprostacyclin-11,15-diacetate is stirred with 16 ml of a mixture of acetic-acid/water/tetrahydrofuran (65/35/10) for 16 h at room temperature and then is vacuum evaporated. Following chromatography of the residue on silica gel, one obtains 400 mg of the title compound as an oil when using ether/acetic-acid (1/1).

IR: 3600, 3410, 2962, 2860, 2200, 1734, 1653, 1240, 970/cm.

EXAMPLE 4

5-cyano-16-,16-dimethyl-18,19-tetradehydroprostacyclin

Similarly to example 1, 0.48 g of 5-cyano-2-descarboxy-2-hydroxymethyl-16,16-dimethyl-18,19-tetradehydroprostacyclin-11,15-diacetate provides 230 mg of the title compound in the form of a colorless oil.

IR: 3600, 3400, 2925, 2200, 1712, 1650, 973/cm.

The initial material for the above title compound is prepared as follows:

(4a)
(1S,5R,6R,7R)-6-[(E)-(3R)-3-benzoyloxy-4,4-dimethyl-1-octene-6-ynyl]-7-benzoyloxy-2-oxabicyclo[3.3.0]-octane-3-one Similarly to example (1a), 1.5 g of (1S,5R,6R,7R)-6-[(E)-3-hydroxy-4,4-dimethyl-1-octene-6-ynyl]-7-benzoyloxy-2-oxabicyclo[3.3.0]-octane-3-one, 6 ml of pyridine and 1.2 ml of benzoyl chloride provide 1.85 g of the title compound in the form of an oil.

IR: 2965, 2925, 1770, 1715, 1600, 1586, 1270, 970/cm.

(4b)
5-cyano-2-descarboxy-2-(dimethyl-tert-butylsilyloxymethyl)-16,16-dimethyl-18,19-tetradehydroprostacyclin-11,15-diacetate Similarly to example (1b), 320 mg of the title compound is obtained in the form of a colorless oil from 1.3 g of the dibenzoate prepared per example (1b).

IR: 2955, 2925, 2200, 1733, 1650, 1240, 972, 835/cm.

(4c)
5-cyano-2-descarboxy-2-hydroxymethyl-16,16-dimethyl-18,19-tetradehydro-prostacyclin-11,15-diacetate Similarly to example (1c), 205 mg of the title compound is obtained from 0.3 g of the diacetate prepared per example (4b).

IR: 3600, 3400, 2960, 2862, 2200, 1732, 1650, 972/cm.

EXAMPLE 5
5-cyano-(15RS)-15-methyl-18,19-tetradehydro-prostacyclin

Similarly to example 1, 370 mg of the title compound is obtained in the form of a colorless oil from 0.7 g of 5-cyano-2-descarboxy-2-hydroxymethyl-(15RS)-15-methyl-18,19-tetradehydro-prostacyclin-11-acetate.

IR: 3610, 3400, 2920, 2200, 1712, 1650, 972/cm.

The initial material for the above title compound is prepared as follows:

(5a)
5-cyano-2-descarboxy-2-(dimethyl-tert-butylsilyloxymethyl)-(15RS)-15-methyl-18,19-tetradehydro-prostacyclin-11-acetate Similarly to example (1b), 920 mg of the title compound is obtained in the form of an oil from 4.7 g of (1S,5R,6R,7R)-6-[(E)-(3RS)-3-hydroxy-3-methyl-1-octene-6-ynyl]-7-benzoyloxy-2-oxabicyclo[3.3.0]-octane-3-one and 8 g of 6-(dimethyl-tert-butylsilyloxy)-hexane nitrile.

IR: 2950, 2925, 2860, 2200, 2733, 1650, 1240, 972, 835/cm.

(5b)
5-cyano-2-descarboxy-2-hydroxymethyl-(15RS)-15-methyl-18,19-tetradehydro-prostacyclin-11-acetate Similarly to example (1c), 0.6 g of the title compound is obtained in the form of a colorless oil from 0.8 g of the acetate prepared per example (5a).

IR: 3600, 3400, 2960, 2860, 2200, 1732, 1651, 1240, 972/cm.

EXAMPLE 6
5-cyano-(16RS)-16,20-dimethyl-18,19-tetradehydro-prostacyclin

A mixture of 0.7 g of 5-cyano-2-descarboxy-2-hydroxymethyl-(16RS)-16,20-dimethyl-18,19-tetradehydro-prostacyclin-11,15-diacetate, 1.9 g of pyridinium dichromate and 10 ml of dimethylformamide is stirred for 30 h at room temperature. It is then diluted with water and extracted with a mixture of ether/pentane (2/1), the organic extract is washed with water, dried over magnesium sulfate and vacuum-evaporated. After filtering the residue on silica gel, 0.5 g of 5-cyano-(16RS)-16,20-dimethyl-18,19-tetradehydro-prostacyclin-11,15-diacetate is obtained using ether/acetic-acid (1/1). The diacetate is stirred for 16 h at room temperature in 24 ml of methanol with 0.6 g of potassium carbonate. Then, it is acidified to a pH of 5 using 10% citric acid, extracted with methylene chloride, the organic extract being shaken with a brine, and dried over magnesium sulfate. The evaporation residue is chromatographed with methylene-chloride/isopropanol (85/5) on silica gel. 310 mg of the tital compound is obtained in the form of a colorless oil.

IR: 3600, 3400, 2925, 2200, 1713, 1651, 973/cm.

The initial material for the above tital compound is prepared as follows:

(6a)
(1S,5R,6R,7R)-6-[(E)-(3S,4RS)-3-benzoyloxy-4-methyl-1-nonene-6-ynyl]-7-benzoyloxy-2-oxabicyclo[3.3.0]-octane-3-one Similarly to example (1a), 4 g of the title compound in the form of an oil is obtained from 3.5 g of (1S,5R,6R,7R)-6-[(E)-(3S,4RS)-3-hydroxy-4-methyl-1-nonene-6-ynyl]-7-benzoyloxy-2-oxabicyclo[3.3.0]-octane-3-one.

IR: 2960, 2925, 1771, 1715, 1602, 1584, 1450, 1315, 1270, 1100, 970/cm.

(6b)
5-cyano-2-descarboxy-2-(dimethyl-tert-butylsilyloxymethyl)-(16RS)-16,20-dimethyl-18,19-tetradehydro-prostacyclin-11,15-diacetate 24.2 ml of a 1.5 molar butyl lithium solution (in hexane) is dripped into 5.2 ml of diisopropylamine at −25° C., the substance is stirred for 1 h and then is reacted with 7 ml of hexamethyl phosphoric acid triamide. A solution of 8.5 g of 6-(dimethyl-tert-butylsilyloxy)-hexane nitrile in 10 ml of tetrahydrofuran is dipped at −70° C. into the above mixture which is then stirred for 20 minutes at −70° C. and reacted with a solution of the dibenzoate prepared per example (12a) in 30 ml of ether and 30 ml of tetrahydrofuran. After 20 minutes, the reaction mixture is acidified by pouring in a 10% citric acid solution to a pH of 5 and extracted with ether, the organic extract is shaken with water, dried over magnesium sulfate and vacuum evaporated. The residue is filtered with acetic acid on silica gel. 3.3 g of the reaction product of the metallo-organic reaction is obtained as a 11,15-diol which is dissolved in 200 ml of ether and stirred with 120 ml of a diluted etheric borotrifluoride solution (prepared per example (1b)) for 1 h at room temperature. Next a 5% sodium bicarbonate solution is poured on, the substance is washed with water until neutral, dried over magnesium sulfate and vacuum evaporated. The residue is stirred for 16 h at room temperature with 12 ml of pyridine and 4 ml of acetic acid anhydride. This is followed by vacuum evaporation and residue chromatography on silica gel. Using hexane/ether (3/2), first 1.4 g of the title compound (5E configuration) is obtained, and then as the more polar component 1.2 g of the isomeric (5Z)-5-cyano-2-descarboxy-2-(dimethyl-tert-butylsilyloxymethyl)-(16RS)-16,20-dimethyl-18,19-tetradehydro-prostacyclin-11,15-diacetate.

IR: 2960, 2935, 2862, 2200, 1732, 1650, 1240, 972, 835/cm.

(6c)
5-cyano-2-descarboxy-2-hydroxymethyl-(16RS)-16,20-dimethyl-18,19-tetradehydro-prostacyclin-11,15-diacetate Similarly to example (1c), 1 g of the title compound in the form of an oil is obtained from 1.3 g of the diacetate prepared per example (12b).

IR: 3600, 3410, 2963, 2860, 2200, 1730, 1650, 1240, 972/cm.

(6d) 3-methyl-2-oxo-oct-5-ynyl-phosphonic acid-dimethylester 120 g of methyl malonic acid diethylester is dripped into a solution of 15.8 g of sodium in 344 ml of ethyl alcohol at room temperature. After 30 minutes 118 g of 1-bromo-2-pentyne (prepared from pent-2-yne-1-ol with phosphorus tribromide in pyridine) is dripped in and the mixture is heated for 16 h with reflux. Then the reaction mixture is filtered, washed with methylene chloride and vacuum evaporated. The residue is dissolved in 500 ml of methylene chloride, shaken twice each time with 50 ml of water, dried by means of magnesium sulfate and vacuum evaporated. The residue is distilled in a 12 torr vacuum. At 135° C., one obtains 147 g of the alkylated methyl malonic acid ester which is heated in 1.2 liters of dimethylsulfoxide and 11 ml of water with 51.6 g of lithium chloride for 4.5 h at the reflux. Then 4.5 liters of ice water is poured on, the substance is extracted with ether, the organic extract is twice shaken with water, dried over magnesium sulfate and vacuum evaporated. The residue distillation at 84° C. and 12 torr provides 82.5 g of 2-methyl-hept-4-yne acid ethylester in the form of a colorless liquid.

646 ml of a 1.52% butyl lithium solution in hexane is dripped into a solution of 176 g of methane phosphonic acid dimethylester in 2 liters of tetra-hydrofuran at −70° C.; the mixture is stirred for 15 minutes and slowly a solution of 82.5 g of 2-methyl-hept-4-yne acid ethylester in 320 ml of tetrahydrofuran is added. This mixture is stirred for 4 h at −70° C., neutralized with acetic acid and vacuum evaporated. The residue is reacted with 200 ml of water, extracted three times with 600 ml of methylene chloride each time, the organic extract is shaken once with 100 ml of water, dried over magnesium sulfate and vacuum evaporated. The distillation of the residue in a 0.6 torr vacuum and at 120° C. yields 85 g of the title compound in the form of a colorless liquid.

(6e)
(1S,5R,6R,7R)-6-[(E)-(4RS)-3-oxo-4-methyl-1-nonene-6-ynyl]-7-benzoyloxy-2-oxabicyclo[3.3.0]-octane-3-one A solution of 8.2 g of the phosphonate prepared in example 6d) in 30 ml of dimethoxyethane is dripped into a suspension of 1.4 g of sodium hydride (50% suspension in oil) in 170 ml of dimethoxyethane; the mixture is stirred for 2 h at room temperature under argon. Next, this mixture is reacted at −20° C. with a solution of 7.6 g of (1S,5R,6R,7R)-6-formyl-7-benzoyloxy-2-oxabicyclo[3.3.0]-octane-3-one in 80 ml of dimethoxyethane, is stirred for 2 h at −20° C., neutralized with acetic acid, diluted with ether, shaken with 4% sodium bicarbonate solution and water, dried over magnesium sulfate and vacuum evaporated. After chromatographing the residue on silica gel and using ether/hexane (6/4), 8.2 g of the title compound is obtained in the form of a colorless oil.

IR: 2962, 2230, 1772, 1718, 1690, 1625, 1600, 975/cm.

(6f)
(1S,5R,6R,7R)-6-[(E)-(3S,4RS)-3-hydroxy-4-methyl-1-nonene-6-ynyl]-7-benzoyloxy-2-oxabicyclo[3.3.0]octane-3-one 3.4 of sodium borohydride is added batchwise to a solution of 6 g of the ketone prepared in example (6e) in 200 ml of methanol, at −40° C., and the mixture is stirred for 1 h at −40° C. under argon. Next it is diluted with ether, washed with water until neutral, dried over magnesium sulfate and vacuum evaporated. By means of column chromatography on silcia gel using ether/hexane (8/2), first 2.6 g of the title compound (3-alpha-hydroxy) is elutriated, next, as the more polar component, 1.9 g of the corresponding isomeric 3 beta-hydroxy compound.

IR (alpha alcohol): 3600, 3500, 2965, 1772, 1718, 1603, 1275, 975/cm.

EXAMPLE 7

(5Z)-5-cyano-(16RS)-16,20-dimethyl-18,19-tetradehydroprostacyclin

Similarly to example 3, 165 mg of (5Z)-5-cyano-2-descarboxy-2-hydroxymethyl-(16RS)-16,20-dimethyl-18,19-tetradehydro-prostacyclin-11,15-diacetate yields 65 mg of the title compound in the form of a colorless oil.

IR: 3610, 3400, 2930, 2200, 1710, 1654, 974/cm.

The initial material for the above title compound is prepared as follows:

(7b)
(5Z)-5-cyano-2-descarboxy-2-hydroxymethyl-(16RS)-16,20-dimethyl-18,19-tetradehydro-prostacyclin-11,15-diacetate.

Similarly to example (3a), 0.29 g of the title compound is obtained in the form of an oil from 0.4 g of (5Z)-5-cyano-2-descarboxy-2-(dimethyl-tert-butylsiloxymethyl)-(16RS)-16,20-dimethyl-18,19-tetradehydro-prostacyclin-11,15-diacetate.

EXAMPLE 8

5-cyano-(16RS)-16-methyl-18,19-tetradehydro-prostacyclin-methylester

A solution of 100 mg of the acid prepared in example 2 is reacted in 10 ml of methylene chloride at 0° C. by dripping it into an etheric diazomethane solution until permanent yellow coloring is achieved. After the solution is vacuum evaporated, the residue is filtered with methylene chloride over a little silica gel and 87 mg of the methylester is obtained in the form of a colorless oil.

IR: 3600, 3410, 2965, 2200, 1732, 1650, 972/cm.

EXAMPLE 9

5-cyano-(16RS)-16,20-dimethyl-18,19-tetrahydro-prostacyclin-methylester

Similarly to the example 8, 120 mg of the acid prepared in example 6 yields 110 mg of the title compound.

IR: 3610, 3400, 2960, 2200, 1732, 1652, 974/cm.

EXAMPLE 10

5-cyano-(16RS)-16-methyl-18,19-tetradehydro-N-methane-sulfonyl-prostacyclin-carboxamide 60 mg of triethylamine is added to a solution of 200 mg of 5-cyano-(16RS)-16-methyl-18,19-tetradehydroprostacyclin-11,15-diacetate (prepared per example 2) in 6 ml of acetonitrile and this mixture is reacted with a solution of 75 mg of methylsulfonyl isocyanate in 4 ml of acetonitrile. This substance is stirred for 4 h at 20° C., vacuum evaporated and reacted with 10 ml of water, neutralized with a 10% citric acid solution and extracted with ether. The organic extract is shaken with brine, dried over magnesium sulfate and vacuum evaporated. The residue is purified by preparative thin film chromatography with methylene-chloride/isopropanol (99/1) and the yield is 172 mg of the methane sulfonyl carboxamide.

This substance is dissolved in 10 ml of methanol to split off the acetate protective groups, reacted with 120 mg of potassium carbonate and stirred for 3 h at 20° C. under argon. Next it is diluted with brine and its pH is adjusted to 7 by means of a 1% citric acid solution; it is extracted with methylene chloride, the extract is shaken with brine, dried over magnesium sulfate and vacuum evaporated. After filtering over silica gel with methylene-chloride/isopropanol (9/1), 85 mg of the title compound is obtained as an oil.

IR: 3600, 3400, 2935, 2865, 2200, 1720, 1651, 1340, 975/cm.

EXAMPLE 11

5-cyano-(16RS)-16,20-dimethyl-18,19-tetradehydro-N-methane-sulfonyl-prostacyclin-carboxamide Similarly to example 10, 280 mg of 5-cyano-(16RS)-16,20-dimethyl-18,19-tetradehydro-prostacyclin-11,15-diacetate yields 106 mg of the title compound in the form of a colorless oil.

IR: 3600, 3410, 2935, 2864, 2200, 1720, 1651, 1340, 973/cm.

EXAMPLE 12

5-cyano-(16RS)-16-methyl-18,19-tetradehydro-N-acetyl-prostacyclin-carboxamide

A solution of 75 mg of triethylamine in 6 ml of acetonitrile is added to a solution of 200 mg of 5-cyano-(16RS)-16-methyl-18,19-tetradehydro-prostacyclin-11,15-diacetate in 6 ml of acetonitrile and a reaction is carried out at 0° C. with a solution of 55 mg of acetylisocyanate in 5 ml of acetonitrile. This mixture is stirred for 2 h at room temperature; it then is vacuum evaporated and reacted with 10 ml of water, adjusted with 1% citric acid to a pH of 7, and extracted with ether. The extract is shaken with brine, dried over magnesium sulfate and vacuum evaporated. After purification by preparative thin-film chromatography on silica gel, the use of methylene-chloride/isopropanol (9/1) yields 100 mg of the title compound in the form of an oil.

IR: 3600, 3400, 2960, 2200, 1731, 1705, 1650, 972/cm.

EXAMPLE 13

5-cyano-(16RS)-16,20-dimethyl-18,19-tetradehydro-N-acetylprostacyclin-carboxamide Similarly to example 12, 170 mg of 5-cyano-(16RS)-16,20-dimethyl-18,19-tetradehydro-prostacyclin-11,15-diacetate (prepared per example 6) yields 85 mg of the title compound in the form of a colorless oil.

IR: 3610, 3400, 2960, 2200, 1732, 1706, 1651, 974/cm.

EXAMPLE 14

Tris-(hydroxymethyl)-aminomethane salt of 5-cyano-(16RS)-16-methyl-18,19-tetradehydro-prostacyclin A solution of 30 mg of tris-(hydroxymethyl)-aminomethane in 0.1 ml of water is added to a solution of 98 mg of 5-cyano-(16RS)-16-methyl-18,19-tetradehydro-prostacyclin (prepared per example 2) in 3 ml of acetonitrile, at 80° C., while stirring; this mixture is stirred for 16 h at room temperature. After the solvent has been separated, 103 mg of the title compound is obtained in the form of a wax-like substance.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 5-cyano-prostacyclin of the formula wherein
$R_1$ is $OR_2$ or $NHR_3$; $R_2$ and $R_3$ each independently is
(a) H, (b) $C_{1-10}$-alkyl, (c) $C_{1-10}$-alkyl substituted by halo, $C_{1-4}$-alkoxy or phenyl, 1-naphthyl or 2-naphthyl each optionally substituted as defined below,
(d) $C_{4-10}$-cycloalkyl, (e) $C_{4-10}$-cycloalkyl substituted by $C_{1-4}$-alkyl, (f) phenyl, 1-naphthyl or 2-naphthyl, (g) phenyl, 1-naphthyl or 2-naphthyl substituted by 1–3 halogen atoms, phenyl, 1–3 alkyl groups of 1–4 C atoms each, or a chloromethyl-, fluoromethyl-, trifluoromethyl-, carboxyl-, hydroxy- or alkoxy-group of 1–4 C atoms, or (h) an aromatic, 5- or 6-membered heterocyclic ring containing one hetero atom which is O, N or S, the remaining atoms being carbon; or $R_3$ is an acyl group of a $C_{1-15}$-hydrocarbon carboxylic or sulfonic acid;

B is straight chain or branched alkylene of 2–10 C atoms;

W is hydroxymethylene or $$-\overset{\underset{\mid}{CH_3}}{\underset{\underset{\mid}{OH}}{C}}-,$$

wherein the OH group may be in the alpha or beta position, and is optionally modified by replacement of the H atom of the OH with an ether or acyl group which is conventional for such replacements in prostaglandins and which is readily cleavable at physiological pH's;

$R_4$ is hydroxy, optionally modified as described for W above;

$R_5$, $R_6$, $R_7$ and $R_8$ each independently is hydrogen, alkyl of 1–5 C atoms of methoxy; and $R_9$ is alkyl of 1–5 C atoms, or for compounds wherein $R_2$ is H, the salts thereof with physiologically compatible bases.

2. A compound of claim 1, wherein W is hydroxy methylene or

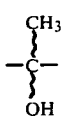

or such a group wherein the H atom of the OH group is replaced by tetrahydropyranyl, tetrahydro-furanyl, alpha-ethoxyethyl, trimethylsilyl, dimethyl-tert-butylsilyl, tribenzylsilyl or $C_{1-4}$-alkanoyl.

3. A compound of claim 1, wherein $R_2$ is $C_{1-4}$-alkyl, phenyl, 1-naphthyl or 2-naphthyl.

4. A compound of claim 1, wherein B is $C_{1-5}$-alkylene.

5. A compound of claim 1, wherein $R_5$, $R_6$, $R_7$, $R_8$ or $R_9$ each is H, methyl or ethyl.

6. A compound of claim 1, wherein $R_1$ is OH, $OCH_3$, $NH_2$, $NHSO_2CH_3$ or $NHCOCH_3$.

7. 5-cyano-18,19-tetradehydro-prostacyclin, a compound of claim 1.

8. 5-cyano-(16RS)-16-methyl-18,19-tetradehydro-prostacyclin, a compound of claim 1.

9. (5Z)-5-cyano-(16RS)-16-methyl-18,19-tetradehydro-prostacyclin, a compound of claim 1.

10. 5-cyano-16,16-dimethyl-18,19-tetradehydro-prostacyclin, a compound of claim 1.

11. 5-cyano-(15RS)-15-methyl-18,19-tetradehydro-prostacyclin, a compound of claim 1.

12. 5-cyano-(16RS)-16,20-dimethyl-18,19-tetradehydro-prostacyclin, a compound of claim 1.

13. (5Z)-5-cyano-(16RS)-16,20-dimethyl-18,19-tetradehydro-prostacyclin, a compound of claim 1.

14. 5-cyano-(16RS)-16-methyl-18,19-tetradehydro-prostacyclin methyl ester, a compound of claim 1.

15. 5-cyano-(16RS)-16,20-dimethyl-18,19-tetradehydro-prostacyclin methyl ester, a compound of claim 1.

16. 5-cyano-(16RS)-16-methyl-18,19-tetradehydro-N-methane-sulfonyl-prostacyclin carboxamide, a compound of claim 1.

17. 5-cyano-(16RS)-16,20-dimethyl-18,19-tetradehydro-N-methane-sulfonyl-prostacyclin-carboxamide, a compound of claim 1.

18. 5-cyano-(16RS)-16-methyl-18,19-tetradehydro-N-acetyl-prostacyclin-carboxamide, a compound of claim 1.

19. 5-cyano-(16RS)-16,20-dimethyl-18,19-tetradehydro-N-acetyl-prostacyclin carboxamide, a compound of claim 1.

20. Tris-(hydroxymethyl)-amino-methane-salt of 5-cyano-(16RS)-16-methyl-18,19-tetradehydro-prostacyclin, a compound of claim 1.

21. A pharmaceutical composition comprising an antihypertensively effective amount of a compound of claim 1 and a pharmaceutically acceptable adjuvant.

22. A pharmaceutical composition of claim 21, wherein the amount of compound of claim 1 is 0.01 to 100 mg.

23. A method of lowering the blood pressure in a host in need of such treatment comprising administering an effective amount of a compound of claim 1 to the host.

* * * * *